(12) United States Patent
Arsenault

(10) Patent No.: US 6,445,945 B1
(45) Date of Patent: Sep. 3, 2002

(54) NON-INVASIVE DETECTION OF ENDOTHELIAL DYSFUNCTION BY BLOOD FLOW MEASUREMENT IN OPPOSED LIMBS USING TRACER INJECTION

(75) Inventor: André Arsenault, 165 rue St-Laurent ouest, Longueil (CA), J4H 1M2

(73) Assignees: André Arsenault, Longueuil (CA); Institut de Cardiologie de Montreal, Montreal (CA)

( * ) Notice: Subject to any disclaimer, the term of this patent is extended or adjusted under 35 U.S.C. 154(b) by 36 days.

(21) Appl. No.: 09/603,554

(22) Filed: Jun. 26, 2000

(51) Int. Cl.⁷ .................................................. A61B 6/00
(52) U.S. Cl. ....................... 600/431; 600/504; 600/407; 600/481; 600/420
(58) Field of Search .................................. 600/504, 507, 600/481, 473, 476, 479, 437, 438, 407, 431, 420, 436

(56) References Cited

U.S. PATENT DOCUMENTS

| | | |
|---|---|---|
| 4,877,599 A | 10/1989 | Lees |
| 5,135,735 A | 8/1992 | Schrader |
| 5,190,744 A | 3/1993 | Rocklage et al. |
| 5,249,124 A | 9/1993 | DeVito |
| 5,256,398 A | 10/1993 | McAfee et al. |
| 5,287,273 A | 2/1994 | Kupfer et al. |
| 5,376,356 A | 12/1994 | Morgan, Jr. |
| 5,377,681 A | 1/1995 | Drane |
| 5,465,284 A | 11/1995 | Karallas |
| 5,494,655 A | 2/1996 | Rocklage et al. |
| 5,590,654 A * | 1/1997 | Prince ......................... 600/431 |
| 5,624,660 A | 4/1997 | Sharp |
| 5,776,063 A * | 7/1998 | Dittrich et al. ............. 600/408 |
| 5,776,093 A | 7/1998 | Goldenberg |
| 5,833,947 A | 11/1998 | Rocklage et al. |
| 5,846,517 A | 12/1998 | Unger |
| 5,886,142 A | 3/1999 | Thakur et al. |
| 5,925,882 A | 7/1999 | Nakamura et al. |
| 5,928,155 A * | 7/1999 | Eggers et al. ................ 600/526 |
| 5,928,625 A | 7/1999 | Dorshow et al. |
| 6,015,384 A | 1/2000 | Ramamurthy et al. |
| 6,219,572 B1 * | 4/2001 | Young ......................... 600/431 |
| 6,233,475 B1 * | 5/2001 | Kim et al. ................... 600/420 |
| 6,295,465 B1 * | 9/2001 | Simonetti .................... 600/413 |
| 6,302,846 B1 * | 10/2001 | Gardner ....................... 600/458 |

OTHER PUBLICATIONS

Gamma Camera Measurement of Limb Blood and its Clinical Application, by Adrian Parkin, IEEE Engineering in Medicine & Biology Society 10th Annual International Conference, 1988. 1 page.

Radionuclide Assessment of Peripheral Hemodynamics: A New Technique for Measurement of Forearm Blood Volume and Flow, by Yasuhiro Todo et al., The Journal of Nuclear Medicine (1986), Febr., No. 2, New York, pp. 192–197.

The Measurement of Limb Blood Flow Using Technetium–Labelled Red Blood Cells, by A. Parkin et al., The British Journal of Radiology, 1986, vol. 59, pp. 493–497.

(List continued on next page.)

Primary Examiner—Kevin Shaver
Assistant Examiner—Navin Natnithithadha
(74) Attorney, Agent, or Firm—Ogilvy Renault; James Anglehart

(57) ABSTRACT

Endothelial dysfunction is a known indicator of cornary artery disease. Endothelial dysfunction is detected by measuring tracer presence in arteries following the release of blood flow into the limb after a period of blockage of blood flow into the limb. The blood flow is measured in a pair of laterally opposed limbs, such as the patient's forearms, and the tracer presence is compared between both limbs. An efficient tracer is a radionuclide and the non-invasive measurement of the radionuclide is carried out by gamma ray detection.

14 Claims, 7 Drawing Sheets

OTHER PUBLICATIONS

Forearm Blood Flow Measurements Using Technetium–99m Human Serum Albumin Following Brachial Arteriotomy, by Adrian Parkin et al., The Journal of Nuclear Medicine, 1989, vol. 30, pp. 45–50.

Article by Celermajer et al, Non–Invasive Detection of endothelia Dysfunction in Children and Adults at Risk of Atherosclerosis, Lancet, 1992, vol. 340, pp. 1111–1115.

Article by Schächinger et al, "Prognostic Impact of Coronary Vasodilator Dysfunction on Adverse Long–Term Outcome of coronary Heart Disease", published in Circulation, 2000, vol. 101, pp. R1 to R8.

Article by Todd J. Anderson, "Assessment and Treatment of Endothelial Dysfunction in Humans", published in vol. 34, Issue 3 (Sep. 1999), pp. 631–638 of JACC.

Article by Celemajer, "Endothelial Dysfunction: Does It Matter? Is It Reversible?", JACC. vol. 30, No. 2, Aug. 1997, pp. 325–333.

Article by Suwaidi et al, "Long–Term Follow–Up of Patients With Mild Coronary Artery Disease and Endothelial Dysfunction", published in Circulation, Jun. 25, 1999, pp. 948–954.

* cited by examiner

Figure 2 (normal hyperaemia)

(abnormal hyperaemia, endothelial dysfunction)

NON-INVASIVE DETECTION OF ENDOTHELIAL DYSFUNCTION BY BLOOD FLOW MEASUREMENT IN OPPOSED LIMBS USING TRACER INJECTION

FIELD OF THE INVENTION

The present invention relates to the diagnosis of endothelial dysfunction, particularly in humans. The non-invasive technique involves blocking blood flow in a limb to stimulate endothelial function and then releasing the blood flow block to observe blood flow which is indicative of endothelial function. More specifically, the present invention relates to a method and apparatus for conducting such measurements by injecting a tracer substance and imaging or otherwise detecting the tracer ingress into the limb following the release of the blood flow block.

BACKGROUND OF THE INVENTION

In recent years, the connection between endothelial dysfunction and the risk of atherosclerosis has been studied and established (see the article by Celermajer et al., "Non-Invasive Detection of Endothelial Dysfunction in Children and Adults at Risk of Atherosclerosis", Lancet, 1992, Vol. 340, pages 1111 to 1115, and the article by Schächinger et al., "Prognostic Impact of Coronary Vasodilator Dysfunction on Adverse Long-Term Outcome of Coronary Heart Disease", published in Circulation, 2000, Vol. 101, pages R1 to R8).

The most popular technique for measuring blood flow for the purposes of endothelial dysfunction in children and adults is the use of Doppler ultrasound which is able to obtain a measurement of blood flow in an artery of a patient non-invasively. As can be appreciated, this requires placing an ultrasound transceiver directly on top of an artery and the measurement accuracy is dependent on proper positioning of the ultrasound equipment with respect to the artery. The paper authored by Todd J. Anderson entitled "Assessment and Treatment of Endothelial Dysfunction in Humans" provides a review of known techniques for assessment of endothelial function in humans. These techniques include intracoronary studies, positron emission tomography, impedance plethysmography, brachial ultrasound (also known as Doppler ultrasound) and venous studies. This article was published in Vol. 34, Issue 3, (September 1999), pages 631–638 of JACC.

SUMMARY OF THE INVENTION

The fact that endothelial dysfunction is an indicator of coronary artery disease (CAD) makes the detection of endothelial dysfunction of great value in the diagnosis and treatment of the general population. People can be at risk of heart disease and CAD as a result of family history, environmental factors (such as the presence of first-hand or second-hand smoke), diet and age. The ability to provide for an efficient non-invasive test for the risk of atherosclerosis would be a valuable tool to determine whether more complex tests are needed to determine the presence of CAD or whether such further tests can be dismissed as unnecessary. Full coronary angiography consumes time on equipment costing in the range of $500,000 to $1,000,000, and require significant operator training and analysis by a skilled specialist. The cost savings to avoiding expensive tests is significant.

The ability to test endothelial dysfunction as an indicator of the state of CAD is also useful for the purposes of monitoring a patient's response to medical treatment, i.e. drugs, diet, exercise, stress management, or a combination thereof.

It would therefore be desirable to provide for a test which would be reliable, easy to carry out, inexpensive and non-invasive for the purposes of determining endothelial dysfunction in humans.

It is an object of the present invention to provide an accurate method and apparatus for detecting endothelial dysfunction in humans which involves a comparatively low cost and is easy to carry out.

According to a first broad aspect of the invention, there is provided a method for diagnosing endothelial dysfunction by measuring tracer presence in arteries following the release of blood flow into the limb after a period of blockage of blood flow into the limb. According to one aspect of the invention, such blood flow is measured in a pair of laterally opposed limbs, preferably the forearms, and the tracer presence is compared between both limbs. The tracer is also preferably a radionuclide and the non-invasive measurement of the radionuclide is carried out by gamma ray detection.

According to another aspect of the invention, there is provided a device for guiding and mounting a person's forearms over a detector measuring tracer presence within a region of interest in the forearm. In one embodiment, the guide is used for holding, in a predetermined position, a person's forearm over a conventional 2-D gamma camera.

According to another embodiment, the guide is used to hold a person's forearm in a fixed position with respect to a detector measuring the tracer presence in which the detector is located within a region of interest and is not required to form a two-dimensional image of the region of interest.

According to yet another embodiment of the invention, a detector for detecting radiation emitted from a radionuclide is provided within a band surrounding a person's limb for detection of radiation.

It will be understood that several embodiments of the invention involve measuring tracer presence in two laterally opposed limbs of a person in which steps are taken to ensure that the sensitivity of measurement between both limbs is the same.

It will also be understood that several embodiments of the present invention involve the injection of a bolus of a radioactive tracer in a vein of a person. Preferably, the dosage strength of the radioactive tracer is measured by a detector prior to injection in order to obtain a reference calibration point. Preferably, the detector used for calibration is the detector used for measuring the tracer in both limbs.

BRIEF DESCRIPTION OF THE DRAWINGS

The present invention will be better understood by way of the following description of preferred embodiments of the invention with reference to the appended drawings in which:

FIG. 7, are rotatably mounted to a forearm support surface wherein the detectors can be rotated to face a support for holding the radioactive bolus between the two detectors equidistantly therebetween;

DETAILED DESCRIPTION OF THE PREFERRED EMBODIMENT

Applicants have tested in a clinical environment the measurement of the presence of a radioactive tracer in two forearms of a patient using a conventional gamma ray or scintillation camera. Such a camera is able to provide an image of the increasing presence of a radioactive isotope entering the arms following the injection of a bolus of the tracer in a vein. In the clinical experiments conducted, the bolus of tracer was injected in a patient's upper arm in a vein which would bring the bolus of tracer to the heart for even distribution to both the left arm and the right arm, with a slight delay for the left arm. For the purposes of testing endothelial dysfunction, blood flow is blocked for a period of time, such as a few minutes to several minutes. The blockage of blood flow in the one arm followed by the subsequent release of the blood flow blockage would lead to a substantially increased blood flow in the arm previously blocked which bodily function is referred to as normal hyperaemia. This function is possible when there is no endothelial dysfunction. It is preferred that the injection of the bolus be administered to the unblocked arm.

Figure 1:
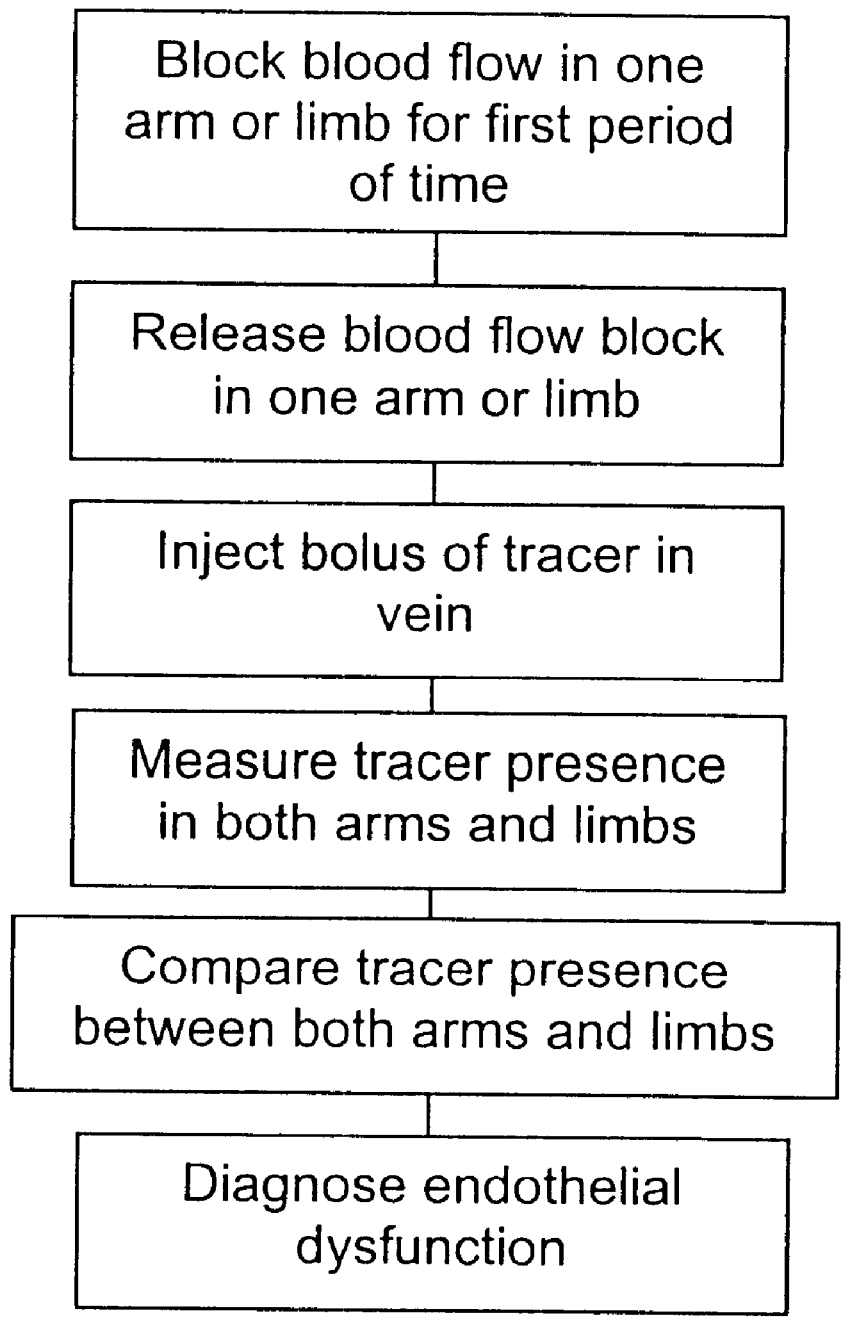
FIG. 1 is flow chart of the method according to the preferred embodiments.
Figure 2:
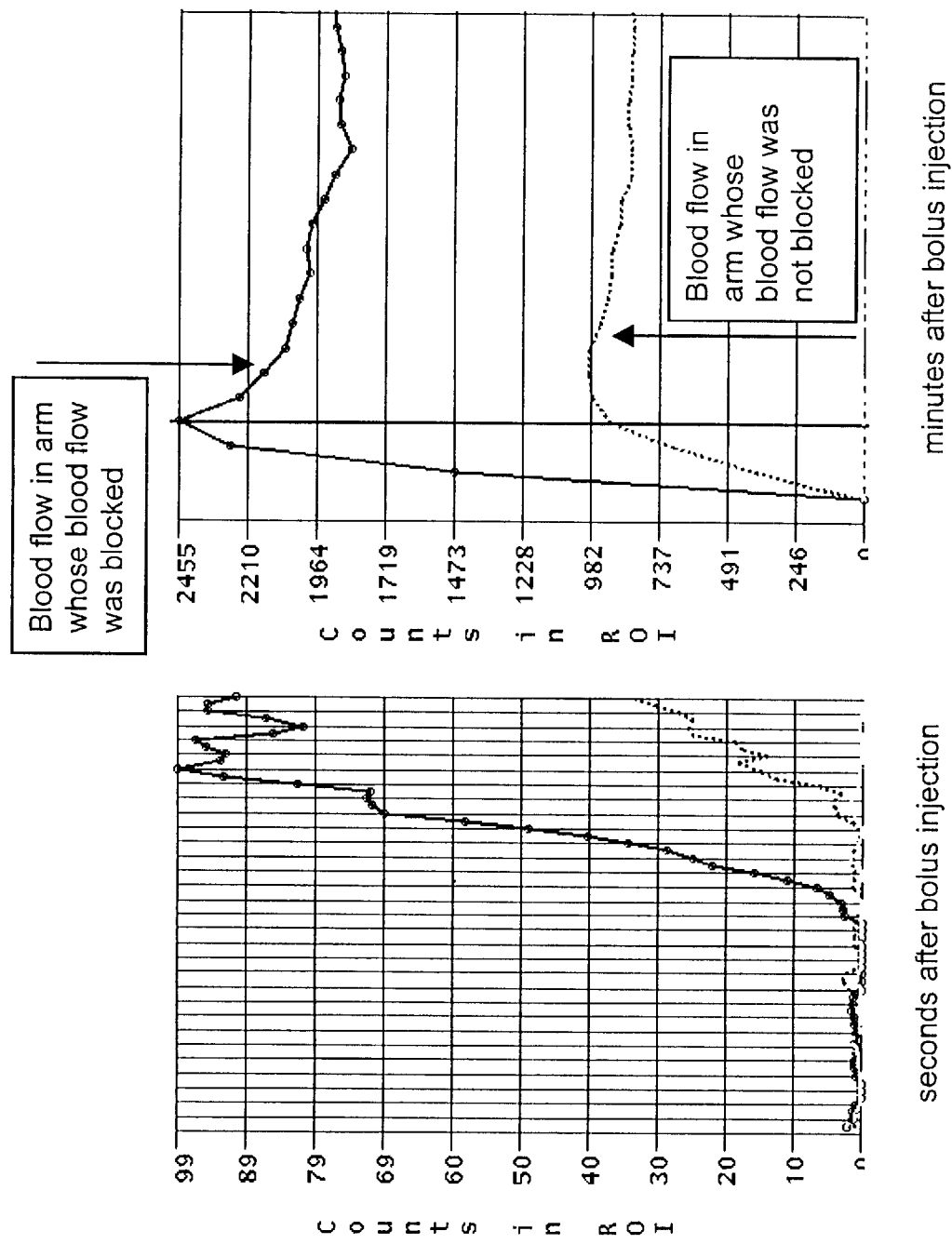
FIG. 2 is a graph obtained from clinical studies of a patient exhibiting normal hyperaemia showing count rate as a function of time, the left-hand graph illustrating an expanded view of the first few seconds after bolus injection and the right-hand graph illustrating the count rate over time extending into a steady state region after several minutes.

In the case of FIG. 2, the healthy patient exhibits a significant rapid increase of blood flow in the arm which was previously blocked.

Figure 3:
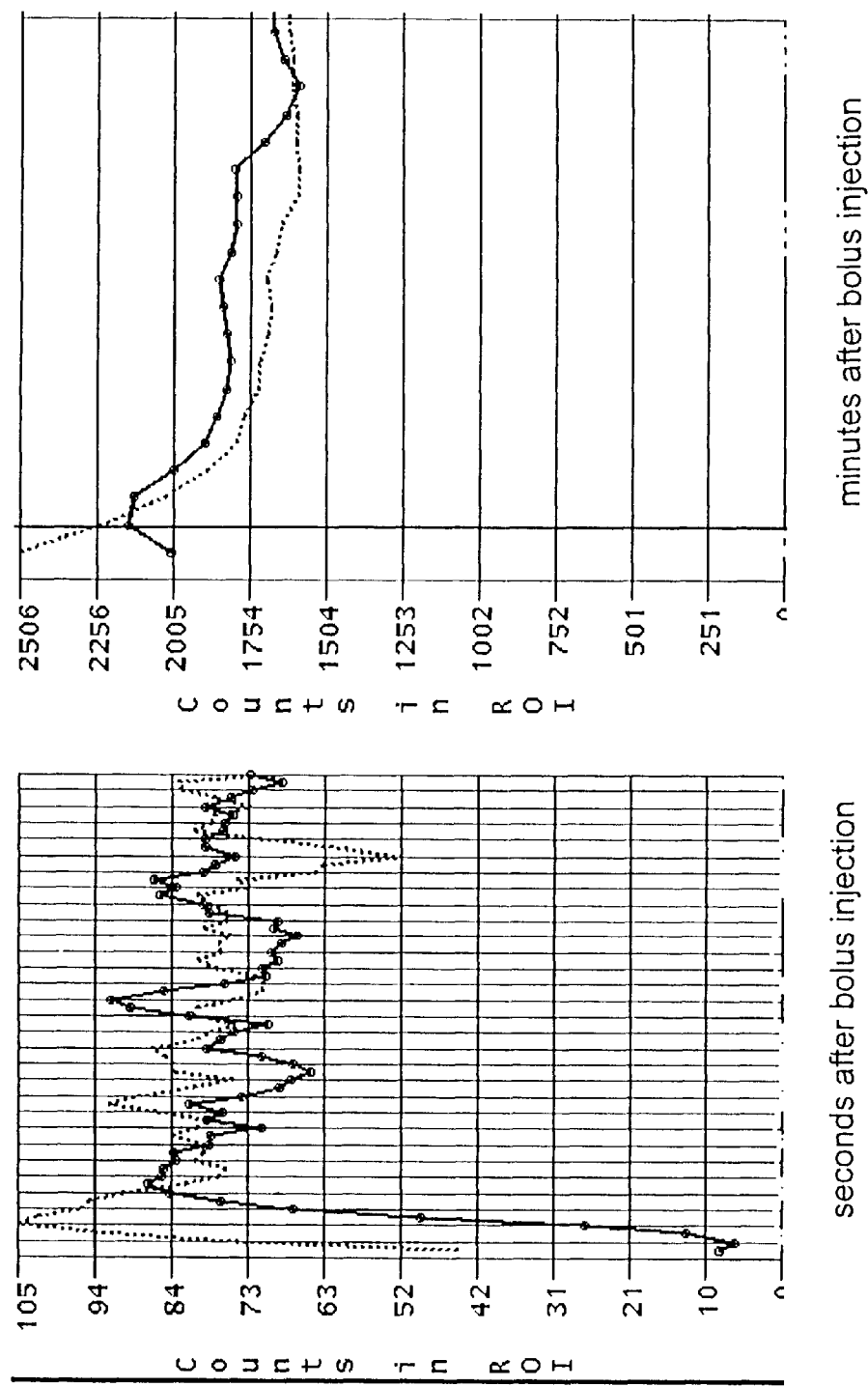
FIG. 3 is a graph similar to FIG. 2 for a patient exhibiting abnormal hyperaemia, i.e. endothelial dysfunction.
Figure 4:
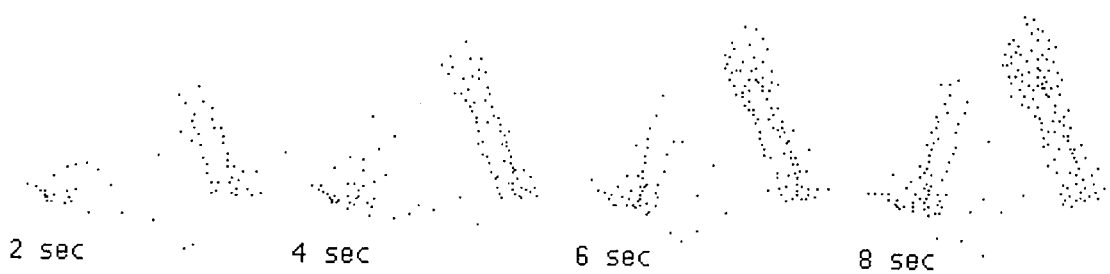
FIG. 4 illustrates a two-dimensional image obtained using a conventional two-dimensional gamma camera of a pair of forearms placed over a gamma camera surface showing the progression of image acquisition over the first 8 seconds in which the imaging of the radioactive isotope flowing in the pair of arteries in each forearm can be clearly seen up until the point that the radioactive isotope penetrates into the tissue of each forearm (the illustration of FIG. 4 corresponds to normal hyperaemia)

As illustrated in FIG. 4, the right-hand arm shows presence of the radioactive tracer at a much greater rate of increase in comparison to the left forearm. The number of counts illustrated in FIGS. 2 and 3 can be measured by integrating the counts found in any particular area within the two-dimensional image acquired using the conventional scintillation camera. The choice of area over which the number of counts is to be integrated is to be chosen taking into consideration a number of factors. Applicants prefer to choose a region which is not too close to the elbow and not too close to the wrist. While the larger the area chosen, the greater number of counts obtained, it may be desirable to choose a restricted area such as an area corresponding to each artery. Applicants have found that choosing a medial area of approximately the width of the forearm and approximately mid-distance between the elbow and the wrist provides satisfactory results. In the data collected in FIG. 4, a patient placed his forearms directly on the scintillation camera screen without the use of a guiding device. Care was therefore taken to select the region of the whole image from each forearm for comparing the tracer presence growth in each of the forearms.

As illustrated in FIG. 3, it is clear that in the case of abnormal hyperaemia, i.e. endothelial dysfunction, the increase in presence of a tracer in both forearms is substantially the same. The significant difference between normal and abnormal hyperaemia allows for a clear diagnosis. In the preferred embodiments, this diagnosis is to be made using the data acquired over time, as illustrated in FIGS. 2 and 3, using a radiation detector capable of accurately resolving the count rate in the region of interest in order to show the shape of the rapid tracer presence growth in the respective forearms. While less desirable, it would be possible within the scope of the present invention to use a tracer presence detector having a much slower response which would be useful in measuring the steady state value reached after a few minutes. Alternatively, it is also within the scope of the present invention to use the measurement of tracer presence in a single limb and to derive sufficient information from such measurement to determine whether normal or abnormal hyperaemia and, therefore, endothelial function occurred in the patient.

It will be appreciated that while detection using a single limb is possible, the advantages of measuring tracer presence in both limbs typically will greatly outweigh any disadvantage in needing to provide more equipment to measure tracer presence in both limbs.

Figure 5:
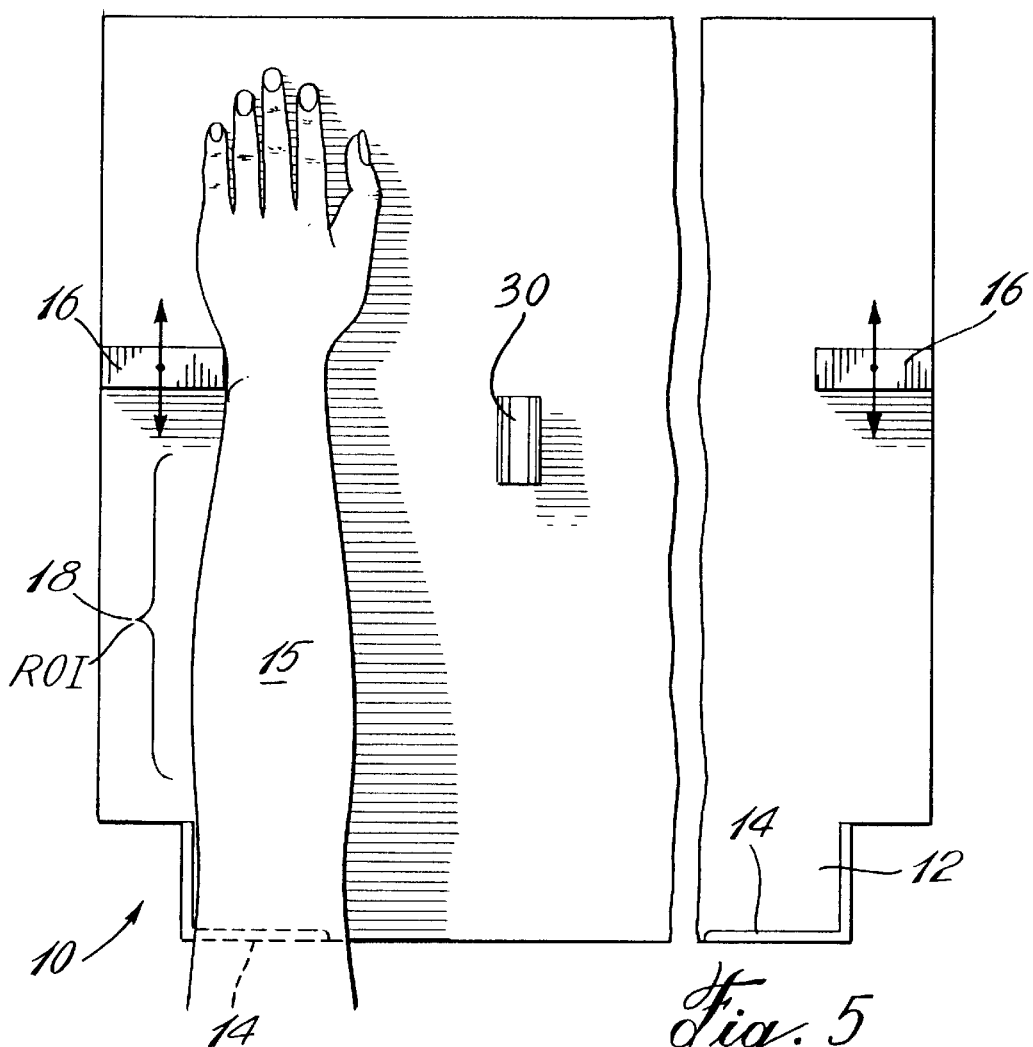
FIG. 5 is a plan view of a forearm support guide for mounting to the surface of a conventional gamma camera according to the first preferred embodiment.
Figure 6:
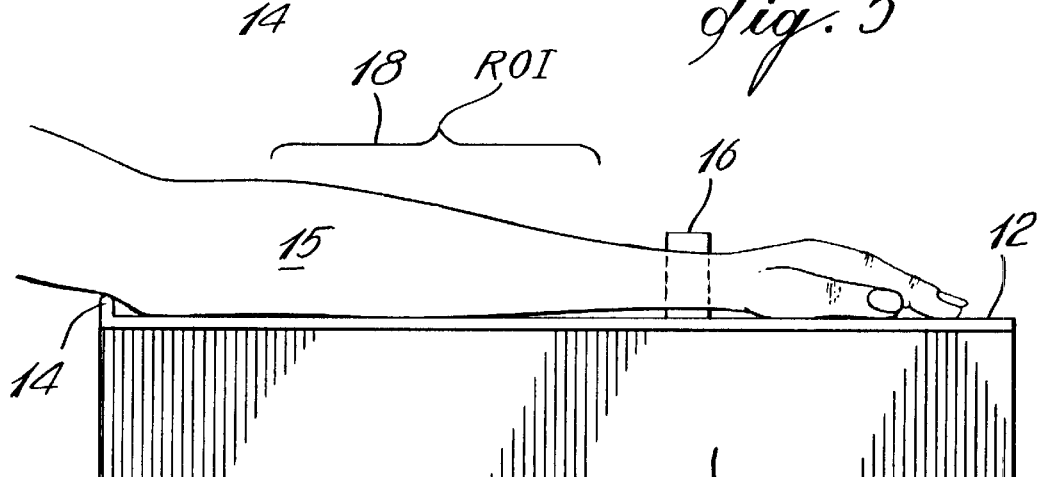
FIG. 6 is a side view of the device according to FIG. 5.

According to the first embodiment illustrated in FIGS. 5 and 6, the apparatus according to the invention 10 comprises a radiotransparent plate 12 able to be fitted over a conventional gamma camera arranged to be level and facing upwards. In order to mount the apparatus 10 to the camera 20, fasteners may be used, or the outer edges of the plate 12 may extend over and downwardly at the sides to be fixed in position while resting on the camera window. Left and right bottom corners 14 have edges for supporting the patient's elbows when pressure is exerted towards the patient and outwardly against the supports 14. To ensure that the patient's arms are in a fixed position, a slidable ulnar support 16 is placed at or just before the wrist. The purpose of choosing the support points in the embodiment of FIG. 5 is to choose locations where the patient can contact the guide device 10 with the bone substantially contacting the guide device, rather than softer tissues such as muscle. In this way, a change in patient pressure against the guide device 10 will not result in a change in forearm position. The forearm 15 includes a region of interest 18 (ROI) which is substantially a middle portion between the elbow and the wrist. In the preferred embodiment, the patient places his or her hands, palms down, on the surface 12 and as illustrated in FIG. 6, the gamma camera 20 is positioned underneath.

It will be noted that the patient's forearms are preferably positioned such that they are extended, i.e. the elbow is bent minimally, in order to reduce any obstruction in the blood flow due to compression at the elbow joint. The patient's forearms are preferably positioned ergonomically on the surface of the camera 20. In the preferred embodiment, the camera is positioned to face upward at a desired height so that the patient may sit on a chair with his or her arms extended and have his or her palms rest comfortably on the camera surface. With control, a patient may keep his forearms in a fixed position on the camera surface without abutment supports 14 and 16. Alternatively, a resilient cover, such as foam material, could be provided and placed over the forearms to help the patient keep his or her forearms in a steady and fixed position on the surface 12. Such a cover could be hinged to the surface 12 and be locked in a covering position for the duration of the test.

Figure 8:
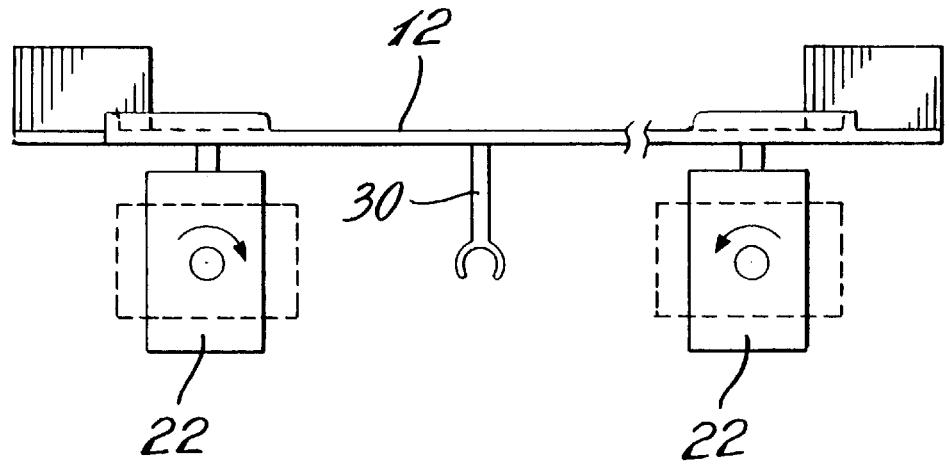
FIG. 8 is a lateral end view of the apparatus according to the third preferred embodiment in which a pair of detectors, as per

As in the embodiment of FIG. 8, the embodiment of FIGS. 5 and 6 may provide for calibration of the bolus to be used. The bolus may simply be placed in a designated region on the surface 12, as provided for by markings or by a holding device 30, e.g. similar to the holding device 30 illustrated in FIG. 8. Since camera may have variation in sensitivity as a function of position, it is important to fix the position of the bolus on the surface 12 for calibration purposes.

Different configurations of abutment supports 14 and 16 can be provided. For example, finger posts, i.e. vertical posts received in the crotch between fingers, may be used to position the hand, while an elbow or lateral forearm abutment can then be used for positioning the forearm. It may also be desirable to position the forearms resting on the ulnar bone and to position the hand using a vertical grip post.

Figure 7:
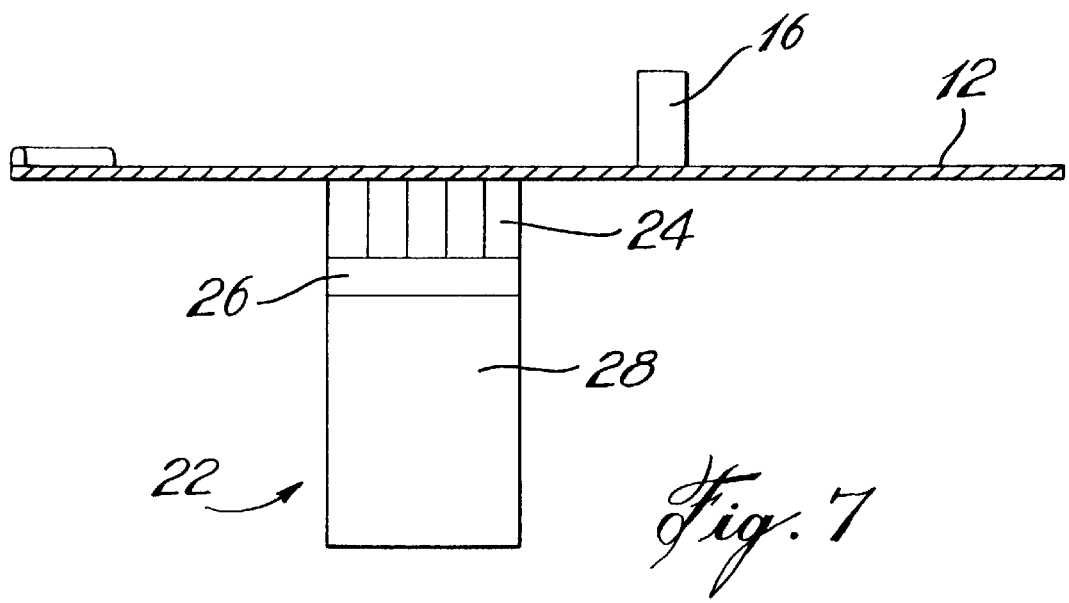
FIG. 7 is a side view of the apparatus according to the second preferred embodiment in which a single scintillation detector is located at the region of interest for a first forearm.

In the embodiment of FIG. 7, the gamma camera 20 is replaced by a single gamma ray detector 22 consisting of a coarse (i.e. large aperture) collimator 24, a scintillation detector material 26, such as a thallium-doped sodium iodide crystal or the like 26, and a photomultiplier tube 28. Collimator 24 is typically made of lead, although steel or any suitable dense metal may be used. The use of shielding and collimation is not as important to the present invention as in the field of nuclear imaging. If background levels are low or consistent between a pair of detectors, then shielding and/or collimation may be reduced or eliminated. Photomultiplier tubes 28 are well known in the art. In the embodiment of FIG. 7, the radiation detector 22 is located in a fixed position with respect to support surface 12 in an area which would be located at the average region of interest for a person's forearm. The position of the radiation detector 22 may also be made to slide linearly in a direction extending between the elbow stop 14 and the ulnar support 16 in order to accommodate patients of different size forearms and/or to provide for an adjustment in the position of the region of interest. To ensure that the region of interest at which radiation is detected is the same for both forearms, detector 22 in the case that it is mobile, is adjusted on one side to be in the same relative position as its complementary detector on the other side.

Although a palms down configuration and an upwardly facing detector is preferred, it may also be desirable to provide a positioning guide for a palms up or palms sideways configuration, either with the hand extended (karate chop) or closed (fist or handle grip). When supporting the forearm on the ulnar bone (palm sideways), it may also be desirable to arrange a pair of horizontally facing detectors on opposite sides of the same forearm.

In the embodiment of FIG. 8, the radiation detectors 22 are provided to be pivotable from a position in which they face the region of interest 18 of the forearm to a position in which they face each other in order to be calibrated using the bolus of radioactive tracer which is to be injected into the patient. The bolus is placed in a holder 30 provided under the surface 12 at a position midway between the two detectors 22. The calibration period may be from a few seconds to over a minute to establish an estimate of the radioactive strength of the bolus to be used. This calibration allows, at the same time, the response or sensitivity of each radiation detector to be checked and for the strength of the radioactive bolus to be measured to provide an important reference point for the subsequent measurements and diagnosis.

Figure 9:
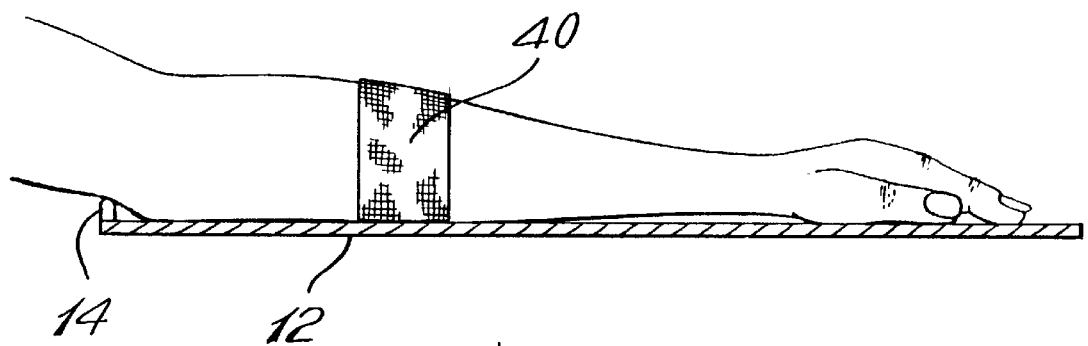
FIG. 9 is a side view of the apparatus according to the fourth preferred embodiment in which a pliable radiation detector is wrapped around the limb.
Figure 10:
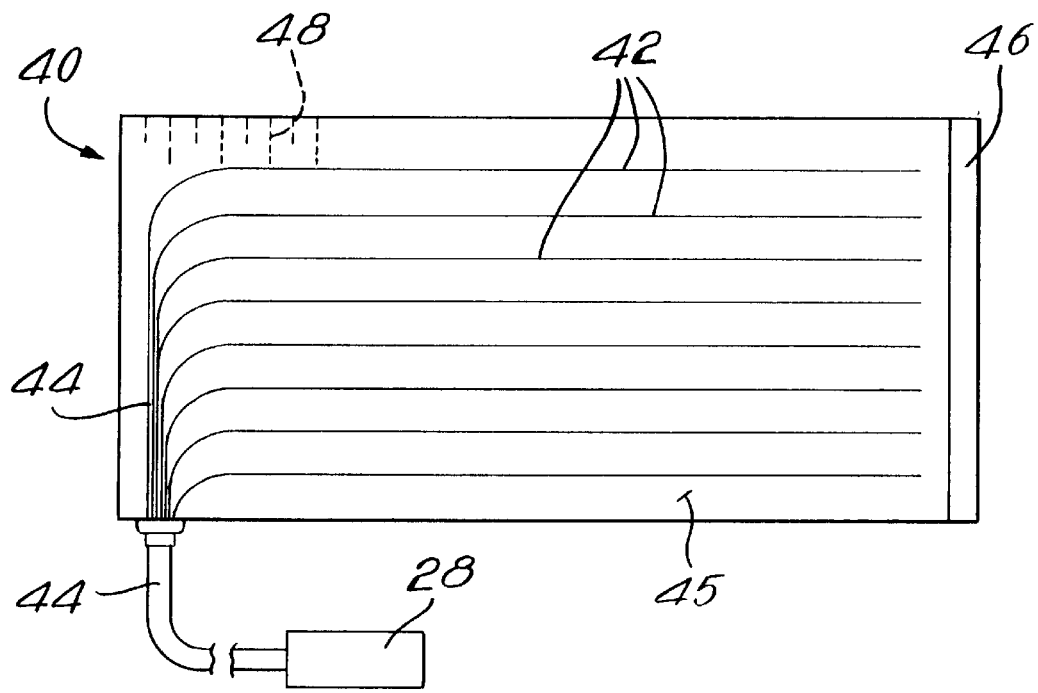
FIG. 10 is a detailed view of the pliable radiation detector according to the fifth preferred embodiment in which scintillation fibers extending circumferentially on the inside of a pliable casing are connected to optical fibers of an optical fiber bundle connected to a light detector or photomultiplier tube (PMT).

In the embodiment of FIG. 9, the radiation detector is provided in a manner which surrounds the limb, such as a leg or a forearm 18. In this embodiment, the radiation detector comprises a plurality of scintillation fibers, as are known in the art, which are arranged within a pliable support 45 to extend circumferentially around the limb without any appreciable pressure which could affect blood flow in the limb. The pliable casing 45 may provide shielding such as a lead blanket or the like. The pliable casing 45 is fastened using a strip of hook and loop type fastener 46 which mates with the complementary material provided on the underside of the pliable casing 45 as illustrated in FIG. 10. To ensure that the position and arrangement of the detector 40 is the same for each limb, it is preferable to provide scale markings or indicia 48 on the outside of the casing to confirm that the strip 46 is wrapped around to the same position on the outside of the pliable casing 45 on each forearm or leg. In keeping with the objective that the casing does not exert any pressure on the limb which could adversely affect blood flow, the casing may be wrapped around the limb and fastened using the fastener 46 as marked by the indicia while being somewhat loose on the limb.

Scintillation light from the fibers 42 is communicated to optical fibers 44 of a bundle which is fed into a common light detector or photomultiplier tube 28. While the detector of FIG. 10 is illustrated as comprising a number of discrete fibers 42, it may alternatively be possible to loop a single fiber 42 in a suitable arrangement, or to use a sufficiently thin film of a plastic scintillator so as to provide a scintillator sheet which is pliable around the limb. The position of the detector 40 with respect to the elbow stop 14 is also a parameter to be controlled during measurement, and scale markings or indicia on the surface of the support plate 12 or the use of a measuring tape may be useful for such purposes.

As an alternative to a soft pliable casing wrapped around a limb, it would be also possible to provide a rigid arcuate casing containing detector material, such as fibers 42. Such an arcuate casing may form a rigid bracelet or a semi-cylindrical member fitting over a limb supported on a surface. In the case of a semi-cylindrical member, the member may be hinged to a support surface. In the case of detecting a radioactive tracer in a person's forearms, the semi-cylindrical casing can be hinged to a support surface as in the embodiment of FIG. 5 or 7 which includes positioning guides for the forearm.

While the preferred embodiments disclose the use of a radioactive tracer for the purposes of measuring blood flow, tracers may also be used to measure blood flow during MRI detection and to enhance detection using conventional techniques such as impedance plethysmography and brachial ultrasound.

It will be appreciated that detectors may be arranged at a variety of different positions and orientations with respect to a limb in a manner suitable to obtain a sufficiently reliable diagnosis of endothelial dysfunction.

The present invention has been described above with reference to a number of specific preferred embodiments. It will be appreciated that many other embodiments are contemplated within the scope of the present invention as defined in the appended claims.

What is claimed is:

1. A method of assessing endothelial dysfunction comprising the steps of:

blocking blood flow in one limb for a first period of time;

releasing the block of blood flow in said one limb;

injecting a bolus of a tracer in a vein such that said bolus is conducted to the heart and evenly distributed to said one limb and an opposed limb via arteries;

measuring a presence of said tracer in said one limb; and analyzing said presence to assess said endothelial dysfunction.

2. The method as claimed in claim 1, wherein said tracer presence is measured and recorded as a function of time.

3. The method as claimed in claim 2, wherein said step of measuring tracer presence comprises measuring tracer presence in both said limbs, further comprising the step of comparing tracer presence between both said limbs.

4. The method as claimed in claim 3, wherein said tracer comprises a radioactive tracer, said step of measuring comprises measuring radiation emitted from a region of interest in said limbs.

5. The method as claimed in claim 4, wherein said tracer presence is measured and recorded as a function of time.

6. The method as claimed in claim 1, wherein said step of measuring tracer presence comprises measuring tracer presence in both said limbs, further comprising the step of comparing tracer presence between both said limbs.

7. The method as claimed in claim 6, wherein said step of measuring comprises adjusting a position of said limbs with respect to a radiation detector so as to detect radiation with a substantially equal sensitivity for each of said limbs.

8. The method as claimed in claim 7, wherein said limbs comprise arms and said region of interest is a forearm.

9. The method as claimed in claim 8, wherein said forearms are placed palms down on a substantially flat surface in order to detect said region of interest of each one of said forearms.

10. The method as claimed in claim 7, wherein diagnosis of endothelial dysfunction is determined from a steady state measurement of radiation detection.

11. The method as claimed in claim 1, wherein said tracer comprises a radioactive tracer, said step of measuring comprises measuring radiation emitted from a region of interest in said limb.

12. The method as claimed in claim 11, wherein said limb is a forearm, and step of measuring comprises providing a gamma camera with its imaging surface ergonomically positioned with respect to a patient, and placing said forearm on said imaging surface of said gamma camera.

13. The method as claimed in claim 12, wherein two said forearms are substantially extended and placed palms down on said imaging surface in order to detect said region of interest of each one of said forearms.

14. The method as claimed in claim 1, wherein said tracer is a radiation emitter, further comprising measuring an activity of said bolus prior to injection to establish a reference activity level.

* * * * *